United States Patent [19]

Gednalske et al.

[11] Patent Number: 5,772,722
[45] Date of Patent: Jun. 30, 1998

[54] METHOD FOR REDUCING ODOR OF MANURE AND REDUCED ODOR MANURE COMPOSITION

[75] Inventors: Joe V. Gednalske, Riverfalls, Wis.; Robert W. Herzfeld, Stillwater, Minn.; William G. Johnson, Columbia, Mo.

[73] Assignee: Cenex/Land O'Lakes Agronomy Company, Arden Hills, Minn.

[21] Appl. No.: 657,020

[22] Filed: May 30, 1996

[51] Int. Cl.⁶ .................................................. C05F 3/00
[52] U.S. Cl. ............................ 71/21; 71/15; 71/DIG. 1; 422/5; 422/34
[58] Field of Search ........................... 422/5, 34; 71/15, 71/21, 901, DIG. 1; 252/DIG. 1

[56] References Cited

U.S. PATENT DOCUMENTS

| | | | |
|---|---|---|---|
| 4,555,063 | 11/1985 | Goettsch | 241/46.04 |
| 5,260,260 | 11/1993 | Gednalske et al. | 504/116 X |
| 5,275,783 | 1/1994 | Menassa et al. | 422/5 |
| 5,463,180 | 10/1995 | Gednalske et al. | 504/323 |

FOREIGN PATENT DOCUMENTS

| | | | |
|---|---|---|---|
| 2902173 | 8/1979 | Germany | 422/5 |

*Primary Examiner*—Fred Teskin
*Attorney, Agent, or Firm*—Kinney & Lange, P.A.

[57] ABSTRACT

An odor reducing blend and a method for reducing odor of manure. The odor reducing blend contains an effective amount of acidulated soybean soapstock and an effective amount of an emulsifier. The method includes providing an odor reducing effective amount of a odor reducing blend. The method also includes mixing the odor reducing blend with manure.

16 Claims, No Drawings

METHOD FOR REDUCING ODOR OF MANURE AND REDUCED ODOR MANURE COMPOSITION

BACKGROUND OF THE INVENTION

The present invention relates to a method for reducing odor of manure. More particularly, the present invention relates to an odor reducing blend and to a method of mixing the odor reducing blend with manure to reduce the odor of manure.

Many types of animal manure, such as from bovine, swine, and poultry, contain nutrients that make it desirable to use manure as an agricultural fertilizer. These nutrients include significant levels of nitrogen, phosphorous, and potassium. Benefits of using manure as a fertilizer include increased soil moisture retention and improved soil structure. These benefits are associated with an increase in soil infiltration rate and a decrease in soil bulk density. Furthermore, using manure as a fertilizer reduces the need to use man-made fertilizers and alleviates problems that are associated with other methods of disposing of manure, such as landfilling.

Manure is typically collected and mixed with water to produce a liquid manure. The liquid manure is then stored in pits on feed lots and dairy farms. The manure pits commonly hold large quantities of liquid manure until it is desired to apply the manure to fields. During storage, heavier solid matter settles to the bottom of the pit while lighter solid matter accumulates as a top layer on the liquid. The liquid manure is periodically agitated to minimize separation and thereby enhance the ability to evenly apply the liquid manure to fields. Prior to plowing the fields, farmers spread the liquid manure over the fields.

In spite of the potential benefits of using manure as a fertilizer, the areas in which manure may be used are limited because many types of manure emit objectionable odors that limit the ability to store manure. Manure pits also frequently generate objectionable odors. None of the prior art techniques reduce the odor of manure to an extent such that manure may be used as a fertilizer on a large scale without objectionable odor.

SUMMARY OF THE INVENTION

The present invention is an odor reducing blend and a method for reducing odor of manure. The odor reducing blend contains an effective amount of acidulated soybean soapstock and an effective amount of an emulsifier. The method includes mixing an odor reducing effective amount of the odor reducing blend with manure.

DETAILED DESCRIPTION OF THE PREFERRED EMBODIMENTS

The present invention includes an odor reducing blend, a method of reducing odor of manure, and a reduced odor manure composition. The odor reducing blend includes a mixture of acidulated soybean soapstock and an emulsifier. The odor of manure is reduced by mixing an effective amount of the odor reducing blend with manure.

The acidulated soybean soapstock is provided in the odor reducing blend at an effective concentration that is between about 20 and 65 percent. Preferably, the effective concentration of acidulated soybean soapstock is approximately 65 percent. Unless referred to otherwise, all references to percent are percent by volume.

The odor reducing blend includes the emulsifier in an effective concentration range. Preferably, the odor reducing blend includes the emulsifier at a concentration range of between about 20 and 60 percent by volume.

Preferred emulsifiers for use with the odor reducing blend of the present invention include an ethoxylated nonylphenol, such as nonoxynol. Examples of ethoxylated nonylphenols that are suitable for use with the present invention include IGEPAL-C0630, which is produced by Rhone-Poulenc of France. However, other emulsifiers may be used alone or in conjunction with nonoxynol in formulating the odor reducing blend of the present invention.

The odor reducing blend may also include a viscosity reducing agent. The addition of the viscosity reducing agent to the odor reducing blend reduces the viscosity of the odor reducing blend to a viscosity that enhances the ease of handling of the odor reducing blend.

The viscosity reducing agent is mixed into the odor reducing blend at an effective concentration of between about 10 and 20 percent. Preferably, the concentration of the viscosity reducing agent is approximately 15 percent. Use of higher levels of viscosity reducing agent is particularly beneficial when using the odor reducing composition at ambient temperatures of less than 50° F.

A preferred viscosity reducing agent is an ethanol-water blend having an ethanol concentration of approximately 70 percent. One suitable ethanol-water blend having an ethanol concentration within this range is a by-product of soybean protein manufacturing processes. The viscosity reducing agent may also be ethanol, isopropanol, or n-butanol.

The odor reducing blend additionally may include water that is provided at an effective concentration of between about 5 and 10 percent, if ethanol, isopropanol or n-butanol is used as a viscosity reducing agent. Using water within this concentration range reduces the cost of formulating the odor reducing blend without reducing the performance of the odor reducing blend. When the ethanol-water blend is used as the viscosity reducing agent, additional water is not required.

The odor reducing blend is preferably fabricated by adding an effective concentration of viscosity reducing agent to an effective concentration of emulsifier. Acidulated soybean soapstock is then added to the viscosity reducing agent-emulsifier dispersion. Once all of the ingredients are sufficiently mixed to provide the odor reducing blend with a substantially homogeneous composition, the odor reducing blend may be stored at ambient temperature without exhibiting changes in consistency or activity. The preferred mixing order and concentrations of the ingredients used in formulating the odor reducing blend are set forth in Table 1.

TABLE 1

| Mixing Order | Ingredient | Concentration (percent) |
| --- | --- | --- |
| 1 | Nonoxynol | 20 |
| 2 | Viscosity Reducing Agent | 15 |
| 3 | Acidulated Soybean Soapstock | 65 |

The acidulated soybean soapstock component is a highly viscous brown liquid having a specific gravity of approximately 0.95 grams per cubic centimeter. When formulating the odor reducing blend, acidulated soybean soapstock is preferably heated to a temperature of at least approximately 72° F. Heating reduces the viscosity of the acidulated soybean soapstock and thereby assists in forming a homogeneous mixture.

The acidulated soybean soapstock is formed by the complete acidulation of soybean soapstock. Soybean soapstock is a by-product of the alkyl refining of soybean oil. In soybean oil processing, crude soybean oil is treated with dilute sodium hydroxide to neutralize the free fatty acids in the crude soybean oil and thereby convert the soybean oil into a soapstock. Alternatively, soda ash may be used alone or in combination with the sodium hydroxide to effect conversion of the crude soybean oil into soapstock. The soapstock is typically separated from the oil by centrifugation or settling. Next, the soapstock is acidulated by the addition of sulfuric acid.

Soybean soapstock is typically produced at a rate of approximately 6 percent of the total volume of the refined crude soybean oil. The free fatty acids in acidulated soybean soapstock are typically less than 1 percent of the total volume of the refined crude soybean oil. Soybean soapstock is also referred to as "foots" since the soapstock accumulates at the bottom of a refining tank. The acidulated soybean soapstock is regarded as a relatively unrefined waste product of soybean oil processing. Because of these characteristics, acidulated soybean soapstock has previously experienced only limited commercial use by soap manufacturers and animal producers.

Contract grade acidulated soybean soapstock includes a total fatty acid concentration of not less than 85 percent. However, the acidulated soybean soapstock preferably has a total fatty acid concentration of between about 94 and 96 percent. Acidulated soybean soapstock also typically includes a moisture level of up to 5 percent. A typical compositional analysis of acidulated soybean soapstock is set forth in Table 2. This compositional analysis was obtained from acidulated soybean soapstock produced by Honeymead Products Co. of Mankato, Minn. A fatty acid profile for this acidulated soybean soapstock material is set forth in Table 3.

TABLE 2

| | |
|---|---|
| Acid value | 80–130 |
| Total fatty acids | 94–96 percent |
| Color | Dark |
| Iodine value | 118–130 |
| Moisture (Karl-Fisher) | <5 percent |

TABLE 3

| Fatty acid profile | Percent of Total Fatty Acids |
|---|---|
| Myristic acid (14:0) | 0.1 |
| Palmitic acid (16:0) | 14.1 |
| Stearic acid (18:0) | 4.8 |
| Oleic acid (18:1) | 21.0 |
| Linoleic acid (18:2) | 52.2 |
| Linolenic acid (18:3) | 6.9 |
| Arachidic acid (20:0) | 0.3 |
| Behenic acid (22:0) | 0.4 |

The nonoxynol used in formulating the odor reducing blend is described in U.S. Pat. No. 2,313,477. Nonoxynol is also known by chemical names that include Δ-(nonylphenyl)-ω-hydroxypoly(oxy-1,2-ethanediyl); polyethylene glycol ether; mono(nonylphenyl) ether; macrogel nonylphenyl ether; polyoxyethylene(n)-nonylphenyl ether; nonylphenyl polyethylene glycol ether; nonylphenoxy polyethoxyethanol; and poly(oxy-1,2-ethanediyl)-Δ-(nonphyenol)-Ω-hydroxy, CAS Registration No. 0009016-45-9. Nonoxynol has the following chemical formula: $C_9H_{19}-(OCH_2CH_2)_nOH$. The "n" in this chemical formula ranges from 8–10 carbon atoms. The "n" is preferably 9 carbon atoms.

As manure is collected, the manure is mixed with water to produce liquid manure using conventionally known techniques. Forming liquid manure assists in evenly applying the manure as fertilizer. The odor reducing blend of the present invention is blended with liquid manure at a concentration that is effective to reduce the odor of the liquid manure as the liquid manure is applied over fields. The odor reducing blend is mixed with liquid manure at an effective concentration of between about 0.1 and 1.0 percent. Preferably, the concentration of the odor reducing blend mixed with manure is approximately 0.25 percent. While the reduced odor manure composition is preferably sprayed over the fields, those with ordinary skill in the art will appreciate that the reduced odor manure composition can be applied to the field using other techniques.

When manure is stored in manure pits for extended periods of time and the odor emitted from the manure pit is objectionable, the odor reducing blend may be mixed with the liquid manure at a concentration that is effective to reduce the odor of the manure. The odor reducing blend is mixed with liquid manure at an effective concentration of between about 0.1 and 1.0 percent. Preferably, the concentration of the odor reducing blend mixed with manure is approximately 0.25 percent.

The following examples are presented to further illustrate the present invention and are invented to limit the scope thereof.

EXAMPLE 1

An odor reducing blend was prepared by mixing nonoxynol with an ethanol-water blend having an ethanol concentration of approximately 70 percent. The nonoxynol and ethanol-water blend were provided at concentrations so that the odor reducing blend had a nonoxynol concentration of approximately 20 percent and an ethanol-water blend concentration of approximately 15 percent.

Acidulated soybean soapstock was heated to a temperature of approximately 72° F. and then mixed with the nonoxynol and ethanol-water blend dispersion to form the odor reducing blend. The concentration of the acidulated soybean soapstock in the odor reducing blend was approximately 65 percent.

A quantity of a swine manure solution was placed into a first jar. The odor reducing blend was mixed into the swine manure solution at a concentration of approximately 0.25 percent. The first jar was placed in a first enclosed room.

A control was prepared by placing swine manure solution in a second jar in a quantity that was approximately equivalent to the quantity of the swine manure solution in the first jar. The control was placed in a second enclosed room.

Twenty-two people were allowed to enter the first and second enclosed rooms. After entering both the first and second enclosed rooms, the people were asked to compare the odor emitted from the jars. Twenty out of twenty-two people indicated that the odor emitted from the first jar was significantly reduced when compared to the odor emitted from the second jar. This test thereby indicates that over 90 percent of the people found that mixing the odor reducing blend with the swine manure solution significantly reduced the odor of the manure.

EXAMPLE 2

The odor reducing blend was prepared using the method set forth in Example 1. A quantity of a swine manure solution, which was different than the swine manure solution utilized in Example 1, was placed into a first jar. The odor reducing blend was then mixed with the swine manure solution at a concentration of approximately 0.25 percent. The first jar was placed in a first enclosed room.

A control was prepared by placing swine manure solution in a second jar in a quantity that was approximately equivalent to the quantity of the swine manure solution in the first jar. The control was placed in a second enclosed room.

Ten people were allowed to enter the first and second enclosed rooms. After entering both the first and second enclosed rooms, the people were asked to compare the odor emitted from the jars. Ten out of ten people indicated that the odor emitted from the first jar was significantly reduced when compared to the odor emitted from the second jar. This test thereby indicates that all of the people found that mixing the odor reducing blend with the swine manure solution significantly reduced the odor of the manure.

Although the present invention has been described with reference to preferred embodiments, workers skilled in the art will recognize that changes may be made in form and detail without departing from the spirit and scope of the invention.

What is claimed is:

1. A method for reducing odor of manure, the method comprising:

providing an odor reducing effective amount of an odor reducing blend having an effective amount of acidulated soybean soapstock and an effective amount of an emulsifier; and mixing the odor reducing blend with manure.

2. The method of claim 1 wherein the concentration of acidulated soybean soapstock in the odor reducing blend is between about 20 and 65 percent by volume.

3. The method of claim 1 wherein the emulsifier is ethoxylated nonylphenol.

4. The method of claim 3 wherein the ethoxylated nonylphenol is nonoxynol.

5. The method of claim 4 wherein the concentration of nonoxynol in the odor reducing blend is between about 20 and 60 percent by volume.

6. The method of claim 1 and further comprising mixing an effective amount of a viscosity reducing agent into the odor reducing blend.

7. The method of claim 6 wherein the viscosity reducing agent is ethanol, isopropanol, n-butanol, or an ethanol-water blend having an ethanol concentration of approximately 70 percent by volume.

8. The method of claim 6 wherein the concentration of the viscosity reducing agent in the odor reducing blend is between about 10 and 20 percent by volume.

9. A reduced odor manure composition comprising manure and an odor reducing effective amount of an odor reducing blend, the odor reducing blend comprising an effective quantity of acidulated soybean soapstock and an effective quantity of an emulsifier.

10. The reduced odor manure composition of claim 9 wherein the concentration of acidulated soybean soapstock in the odor reducing blend is between about 20 and 65 percent by volume.

11. The reduced odor manure composition of claim 9 wherein the emulsifier is ethoxylated nonylphenol.

12. The reduced odor manure composition of claim 11 wherein the ethoxylated nonylphenol is nonoxynol.

13. The reduced odor manure composition of claim 12 wherein the concentration of nonoxynol in the odor reducing blend is between about 20 and 60 percent by volume.

14. The reduced odor manure composition of claim 9 wherein the odor reducing blend further comprises an effective amount of a viscosity reducing agent.

15. The reduced odor manure composition of claim 14 wherein the viscosity reducing agent is ethanol, isopropanol, n-butanol, or an ethanol-water blend having an ethanol concentration of approximately 70 percent by volume.

16. The reduced odor manure composition of claim 14 wherein the concentration of the viscosity reducing agent in the odor reducing blend is between about 10 and 20 percent by volume.

* * * * *